United States Patent
Yazawa et al.

[11] Patent Number: 6,045,699
[45] Date of Patent: Apr. 4, 2000

[54] METHOD OF FILTERING BLOOD

[75] Inventors: Kenichiro Yazawa, Asaka; Fumio Sugaya, Minami-Ashigara; Masao Kitajima, Asaka, all of Japan

[73] Assignee: Fuji Photo Film Co., Ltd., Kanagawa, Japan

[21] Appl. No.: 09/118,633

[22] Filed: Jul. 17, 1998

[30] Foreign Application Priority Data

Jul. 18, 1997 [JP] Japan .................................. 9-193783

[51] Int. Cl.[7] .................................................. B01D 61/22
[52] U.S. Cl. ........................ 210/637; 210/650; 210/741; 210/808; 436/178
[58] Field of Search .................................. 210/490–492, 210/503–506, 508, 637, 645, 650, 651, 741, 808, 767; 422/101; 436/170, 177, 178

[56] References Cited

U.S. PATENT DOCUMENTS

| | | | |
|---|---|---|---|
| 4,477,575 | 10/1984 | Vogel et al. | 436/170 |
| 4,619,639 | 10/1986 | Nose et al. | 604/4 |
| 4,810,394 | 3/1989 | Masuda | 210/767 |
| 5,139,685 | 8/1992 | de Castro et al. | 210/767 |
| 5,423,989 | 6/1995 | Allen et al. | 210/650 |
| 5,460,777 | 10/1995 | Kitijima et al. | 436/170 |
| 5,876,605 | 3/1999 | Kitajima et al. | 210/650 |

FOREIGN PATENT DOCUMENTS

| | | |
|---|---|---|
| 0076665 | 4/1913 | European Pat. Off. . |
| 0785012 | 7/1997 | European Pat. Off. . |
| 0785430 | 7/1997 | European Pat. Off. . |

Primary Examiner—Joseph W. Drodge
Attorney, Agent, or Firm—McAulay Nissen Goldberg Kiel & Hand, LLP

[57] ABSTRACT

This invention provides a method of filtering blood using a filtering material comprising glass fiber filter, capable of obtaining a desired amount of plasma or serum without hemolysis and leakage of blood cells easily which comprises keeping pressure difference between blood inlet side and filtrate outlet side 50 mmHg or less at least for 5 seconds from contacting the blood to be filtered, and keeping the pressure difference 200 mmHg or less throughout the filtering of the blood.

7 Claims, 3 Drawing Sheets

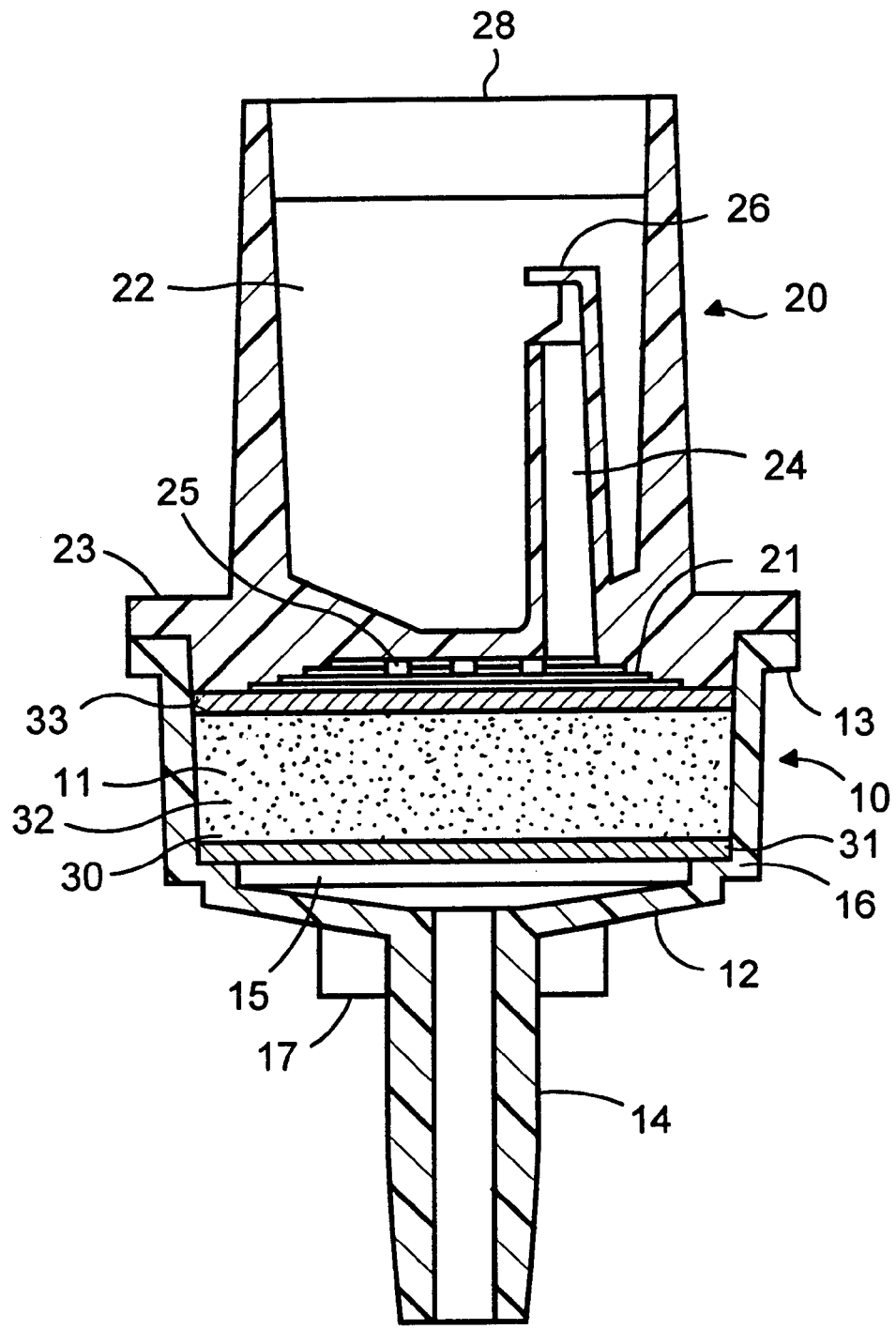
F I G. 2

METHOD OF FILTERING BLOOD

BACKGROUND OF THE INVENTION

This invention relates to a method of filtering blood for preparing a plasma or serum sample from whole blood.

The type or concentration of blood components, such as metabolites, proteins, lipids, electrolytes, enzymes, antigens, and antibodies, is measured, in general, using a plasma or serum sample obtained by centrifuging whole blood. However, centrifuging takes labor and time. Particularly, centrifuging is unsuitable for an urgent case of measuring a small number of samples promptly and in site inspection, because of requiring a centrifuge and electricity. Thereupon, it has been investigated to separate serum from whole blood by filtration.

Several filtration methods using glass fiber filter have been known wherein whole blood is charged into the, glass fiber put in a column from one side of the column, and pressurized or evacuated to obtain plasma or serum from the other side (Japanese Patent KOKOKU Nos. 44-14673, 5-52463, Japanese Patent KOKAI Nos. 2-208565, 4-208856).

However, practical filtration methods capable of obtaining an amount of plasma or serum from whole blood necessary for measuring by an automatic analyzer have not been developed except a part of items, such as blood sugar.

On the other hand, the inventors developed a blood filter unit composed of a filter holder and a syringe. The filter holder is composed of a holder body which contains filter material and a cap which is screwed on the holder body. The filter material consists of, e.g. two sheets of glass fiber filter, one sheet of cellulose filter and one sheet of polysulfone microporous membrane (FIG. 1 of EP 785430 A1).

Another blood filter unit composed of a holder body and a cap was also developed. The holder body consists of a plasma receiver located on the upper side and a filter chamber located on the underside. The filter material put in the filter chamber is composed of six sheets of glass fiber filter and one sheet of polysulfone microporous membrane (Example 1 of EP 785012A1).

Generally, in blood filtration, it is difficult to obtain a necessary amount of plasma or serum by surface filtration wherein blood cells do not enter the inside of filtering material, because flexible blood cells covet the surface of the filtering material in a short time. On thee other hand, in the filtration using glass fiber filter or the likes depth filtration occurs wherein blood cells are entangled in glass fiber with permeating into the glass fiber filter in the depth direction. In the case of the blood filtration using glass fiber filter or the like, leakage of blood cells occurs occasionally at early stage of the filtration. It is also a problem that breakage of blood cells, i.e. hemolysis, tends to occur during filtering.

A great problem in blood filtration is the breakage of blood cells, and several reports concerning the problem have been made. However, any filtration technique capable of measuring potassium ion accurately, which varies by a very small amount of hemolysis, has not been reported.

The measurement of potassium ion is one of the most important items in clinical assay, and potassium ion is frequently measured. The potassium ion concentration of plasma of healthy persons is about 4 meq/L, and an slippage of only about 0.3 meq/L makes exact diagnosis difficult. Accordingly, measuring accuracy required is very high. Since blood cells contain potassium ions in an amount about 40 times as much as plasma, in order to measure potassium ion concentration of plasma at the practical level in viewpoint of clinical diagnosys, it is necessary to prevent breakage of blood cells and escape of potassium ion through blood cell membrane.

It is possible to obtain a very small amount (several tens μl) of plasma by blood filtration using microporous membrane or glass fiber filter. However, when several hundreds μl plasma is separated as disclosed later, blood cells are deformed and broken upon trapped by the pore of filtering material. As a result, accurate measurement is impossible due to the increase of potassium ion concentration of plasma obtained by the filtration.

SUMMARY OF THE INVENTION

An object of the invention is to provide a method of filtering blood capable of obtaining plasma or serum in quantity without hemolysis in a simple manner.

Another object of the invention is to provide a method of filtering blood to obtain a sufficient amount of plasma or serum capable of obtaining accurate value of potassium ion concentration.

The inventors investigated eagerly in order to achieve the above objects, and found that, in conventional suction filtration, permeation of blood into the glass fiber filter begins prior to spreading the blood over the whole surface of the glass fiber filter, and thereby, leakage of blood cells is accelerated, and clogging of the filter by blood cells tends to occur. When suction is continued under the above conditions in order to take a necessary amount of plasma, blood cells are broken by the increase of suction power. Thereupon, they further investigated and devised a filtration system wherein blood filtration is started at a low suction power to spread blood over the whole surface of glass fiber filter and then, suction power is elevated so as not to exceed a prescribed value. According to the system, a desired amount of plasma or serum can be obtained easily in a short period without leakage of blood cells and hemolysis. The present invention was achieved by the finding that control of pressure difference between blood inlet side and filtrate outlet side is very important. The above matters are also effective in the case of pressure filtration.

Thus, the present invention provides a method of filtering blood using a filtering material comprising glass fiber filter, which comprises keeping pressure difference between blood inlet side and filtrate outlet side 50 mmHg or less at least for 5 seconds from contacting the blood to be filtered, and keeping the pressure difference 200 mmHg or less throughout the filtering of the blood.

In the above method, by detecting the pressure difference between blood inlet side and filtrate outlet side, and then controlling a suction and/or pressuring speed according to the pressure difference, blood filtration can be automated or semiautomated, and thereby, burden of workers can be decreased,

BRIEF DESCRIPTION OF DRAWINGS

FIG. 2 is a longitudinal section of a blood filter unit used in the examples of the invention.

Figure 1:
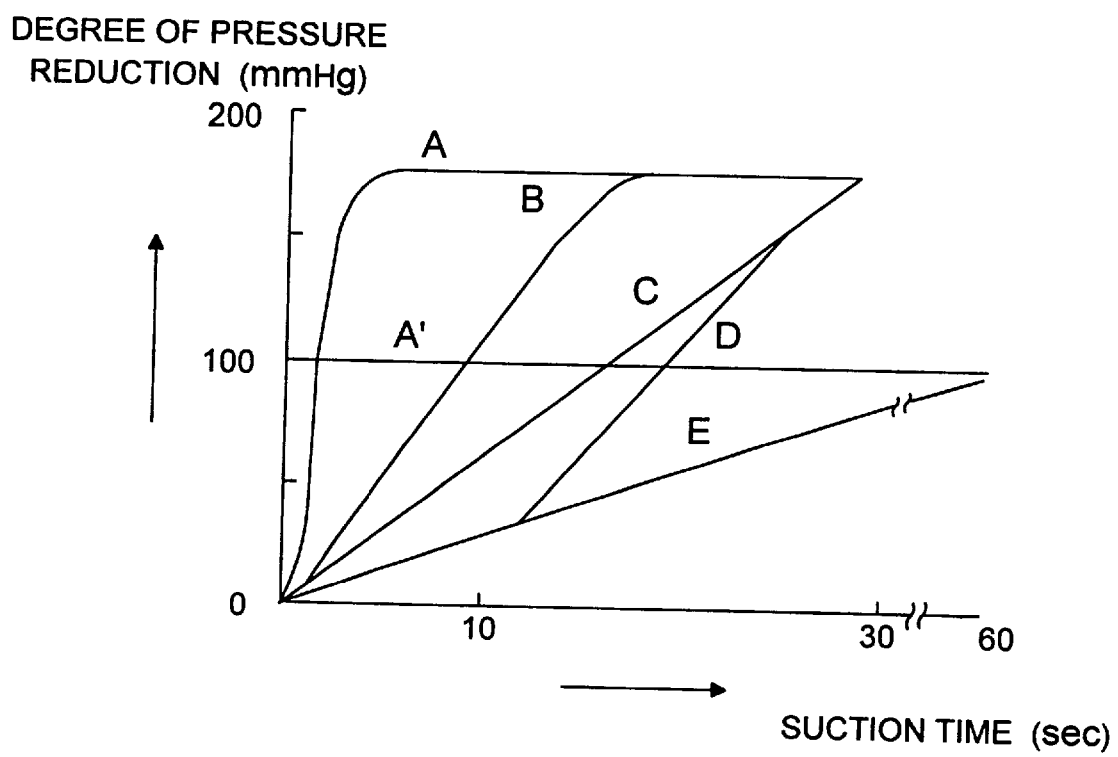
FIG. 1 is a graph illustrating various suction patterns.

10 . . . Holder body
11 . . . Filter chamber
12 Disc portion
13 Flange

14 . . . Blood inlet
15 . . . Space
16 . . . Spacer
17 . . . Flap
20 . . . Cap
21 . . . Step
22 . . . Plasma receiver
23 . . . Flange
24 . . . Plasma passage
25 . . . Projection (Adhering inhibition means)
26 . . . Pent-roof
27 . . . Partition wall
28 . . . Suction port
30 . . . Blood filtering material
31 . . . Nylon mesh
32 . . . Glass fiber flake layer
33 . . . Polysulfone microporous membrane

DETAILED DESCRIPTION OF THE INVENTION

The blood filtering material may be glass fiber filter alone or a combination of glass fiber filter and a microporous membrane or the like. The glass fiber filter can be divided into low density ones and high density ones, and the glass fiber filters used for depth filtration are mainly low density ones. The filtering material used in the invention may be low density glass fiber filter alone, and in this case, it is necessary to care the relation between the void volume of glass fiber filter and the supply amount of blood so that blood cells are not leaked.

As mentioned above, glass fiber filters can be divided into two groups.

The first group functions mainly depth filtration, i.e. blood cells are trapped gradually with permeating in the depth derection of glass fiber filter. The glass fiber filters belonging to this group have a density of about 0.05 g/cm$^3$ to 0.13 g/cm$^3$, a diameter of fiber of about 10 $\mu$m or less, a retaining particle size of about 0.6 $\mu$m or more, and a water permeation speed of about 0.7 ml/sec or more. Among commercial products, Whatman GF/D, Advantec GA-100 and GA-200 and the like belong to this group. Hereafter, the glass fiber filter of this group is called low density glass fiber filter.

The second group glass fiber filters functions to trap blood cells escaped from the low density glass fiber filter, and have a density of about 0.14 g/cm$^3$ or more, a retaining particle size of about 0.5 $\mu$m/sec or less and a water permeation speed of about 0.5 ml/sec or less. Among commercial products, Whatman GF/B, GF/C and GF/F, Advantec (GC-50, GF-75, GB-140, QR-100 and the like belong to this group. Hereafter, the glass fiber filter of this group is called high density glass fiber filter.

Principal glass fiber filter in blood filtering material is the low density glass fiber filter.

By treating the surface of glass fibers with a hydrophilic polymer as disclosed in Japanese Patent KOKAI Nos. 2-208565, 4-208856, filtration can be carried out more rapidly and smoothly. Lectin or other reactive reagents or a modifier may be added to glass fiber, or glass fiber may be directly treated with one or more of them. The glass fiber filter may be composed of laminated or superposed plural sheets.

The filtering materials used in the invention may be integrated by an adhesive which is allocated partially, such as dotted, as disclosed in Japanese Patent KOKAI Nos. 62-138756-8, 2-105043, 3-16651, etc.

The quantity of whole blood filterable by this system is greatly influenced by the void volume existing in glass fiber filter and the volume of blood cells in the whole blood. When the density of the glass fiber filter is high (pore size to retain particles is small), erythrocytes are trapped in the vicinity of glass fiber filter surface, voids in the glass fiber filter are clogged in a very thin region from the surface, and accordingly, filtration does not proceed thereafter. As a result, recovered plasma volume by filtration is small. On that occasion, when the filter material is sucked by stronger suction in order to increase recovered plasma volume, blood cells are destroyed, i.e. hemolyzed. That is, the filtration becomes similar to surface filtration, and utilization rate of void volume of the filter is low.

As an indicator corresponding to void volume or filtrate volume of plasma, water permeation speed is suitable. The water permeation speed is determined by putting a glass fiber filter with a definite area in a closed filter unit of which the inlet and outlet can be connected by a tube, adding a definite volume of water, and pressurizing or sucking it a constant pressure. The water permeation speed is filtrate volume per unite area and time, and expressed by ml/sec.

For example, glass fiber filter 20 mm $\phi$ in diameter is put in a filter unit, and a 100 ml syringe containing 60 ml water is connected to the top of the filter unit. Water flows down naturally, and volume of water passing through the glass filter from 10 sec to 40 sec after starting is measured as the water permeation volume, and the water permeation speed per unit area is calculated from it.

A suitable thickness of the low density glass fiber filter varies according to the plasma volume to be recovered and the density (void content) and area of the glass fiber filter. A necessary amount of plasma for analyzing plural items using dry analytical elements is 100 to 500 $\mu$l. In practical viewpoint, glass fiber filter having an area of 1 to 5 cm$^2$ is suitable. In this case, a suitable thickness of the glass fiber filter is about 1 to 10 mm, preferably about 2 to 8 mm, more preferably about 3 to 6 mm. The above thickness can be made by superposing 1 to 10 sheets, preferably 2 to 6 sheets of glass fiber filter.

Cut pieces of the low density glass fiber filter can be used for a part or the whole of the low density glass fiber layer of the blood filtering material. One sheet of the glass fiber filter has a thickness of about 0.2 to 3 mm, usually about 0.5 to 2 mm. The sheet is cut into pieces having a side or diameter of about 10 to 30 mm, preferably about 15 to 25 mm. The shape of the cut pieces may be square, rectangle, triangle, circle or any other shape. Fundamentally, it is preferable to use the whole body of the glass fiber filter, and accordingly, in the case of circle pieces, recessed arc-shaped pieces are also used. A common shape is quadrangle having a long side/short side ratio of about 1.0 to 5.0, preferably 1.0 to 2.5.

The cutting may be conducted by using a commercial cutter.

It is not necessary to care fiber direction of cut pieces upon charging into a filter chamber.

It is preferable to incorporate a microporous membrane on the filtrate outlet side of the glass fiber filter in order to accelerate the separation of blood cells and plasma and to inhibit the escape of blood cells.

The surface of the microporous membrane has been made hydrophilic, and it has blood cell-separating ability. The microporous membrane can separate whole blood into blood cells and plasma specifically without hemolysis to the degree of substantially influencing analytical values. A suitable pore size of the microporous membrane is smaller than the retaining particle size of glass fiber filter, and is 0.2 $\mu$m or more, preferably about 0.3 to 5 $\mu$m, more preferably about 0.5 to 4.5 μm, particularly preferably about 1 to 3 μm. The void content of the microporous membrane is preferably higher, and a suitable void content is about 40 to 95%, preferably about 50 to 95%, more preferably about 70 to 95%. Illustrative of the microporous membranes are polysulfone membrane fluorine-containing polymer membrane, cellulose acetate membrane, nitrocellulose membrane, etc. The surface of the membrane may be hydrolyzed or may be rendered hydrophilic by a hydrophilic polymer or an activating agent.

As the fluorine-containing polymer membrane, there are the microporous matrix membrane (microporous layer) composed of polytetrafluoroethylene fibrils (fines) disclosed in WO 87/02267, Gore-Tex (W. L. Gore and Associates), Zitex (Norton), Poreflon (Sumitomo Denki), etc. Other fluorine-containing polymer sheets usable as the microporous layer include polytetrafluoroethylene microporous membranes disclosed in U.S. Pat. No. 3,368,872 (Examples 3 and 4), U.S. Pat. No. 3,260,413 (Examples 3 and 4), U.S. Pat. No. 4,201,548, etc., polyvinylidenefluoride microporous membranes disclosed in U.S. Pat. No. 3,649,505 and the like. The microporous membrane of fluorine-containing polymer may be prepared by using a single fluorine-containing polymer or blending two or more kinds of fluorine-containing polymers or further blending one or more polymers not containing fluorine or fibers therewith. As the structure, there are unstretched one, uniaxially stretched one, biaxially stretched one, nonlaminated single layer type, laminated double layer type, such as a membrane laminated to another membrane structure such as a fiber membrane. In the case of nonlaminated type microporous membrane having fibril structure or having been uniaxially or biaxially stretched, microporous membrane having a great void content and a short filtering pass can be prepared by stretching. In microporous membranes having short filtering pass, clogging rarely occurs by solid components (mainly red blood cells) in blood, and the separation time of blood cells and plasma is short. As a result, accuracy in quantitative analysis is improved. The adhesive strength of adhesive used for the partial adhesion to the adjacent microporous membrane can be strengthened by providing the physical activation (preferably glow discharge or corona discharge) disclosed in U.S. Pat. No. 4,783,315 on at least one side of the microporous membrane of fluorine-containing polymer to render hydrophilic.

It is wellknown that fluorine-containing polymer microporous membranes as it is have a low surface tension. As a result, when the membrane is used as the blood cell filtering layer, aqueous liquid samples are repelled and do not diffuse nor permeate over the surface or into the inside. In the invention, the above repelling problem has been resolved by incorporating a sufficient amount of surfactant for rendering the outer surface and the inner space surface of the fluorine-containing polymer microporous membrane substantially hydrophilic thereinto. In order to impart a hydrophilic property sufficient for diffusing, permeating or moving an aqueous liquid sample over the surface or into the inside of the fluorine-containing polymer microporous membrane without repelling to the membrane, in general, it is necessary that the space surface of the membrane is coated with a surfactant in an amount of about 0.01 to 10%, preferably about 0.1 to 5%, more preferably about 0.1 to 1% of the void volume of the membrane. For example, in the case of a fluorine-containing polymer microporous membrane 50 μm in thickness, a preferred amount of surfactant to be impregnated is usually in the range of 0.05 to 2.5 g/m$^2$. As the method of impregnating surfactant into a fluorine-containing microporous membrane, a common method comprises immersing the fluorine-containing microporous membrane, in the surfactant solution dissolved in a low boiling point (a preferable boiling point is in the range of about 50° C. to about 120° C. organic solvent (e.g. alcohols, esters, ketones) to permeate into the inner spaces of the membrane substantially sufficiently, taking the membrane out of the solution slowly, and then drying by blowing air (preferably warm air).

As the surfactant for rendering the foluorine-containing polymer microporous membrane hydrophilic, the surfactant may be nonionic, anionic, cathionic or ampholytic. However, nonionic surfactants are advantageous for the multilayer analytical elements for analyzing whole blood samples, because nonionic surfactants have a relatively low hemolytic activity among the above surfactants.

Suitable nonionic surfactants include alkylphenoxypolythoxyethanol, alkylpolyether alcohol, polyethyleneglycol moneoester, polyethyleneglycol diester, higher alcohol-ethylene oxide adduct (condensate), polyol ester-ethylene oxide adduct (condensate), higher fatty acid alkanol amide, etc.

Examples of the nonionic surfactant are as follows:

As the alkylphenoxypolyethoxyethanol, there are isooctylphenoxypoly-ethosyethanols (Triton X-100; containing 9–10 hydroxyethylene units on average. Triton X-45; containing 5 hydroxyethylene units on average) and nonylphenoxypolyethoxyethanols (IGEPAL CO-630; containing 9 hydroxyethylene units on average, IGEPAL CO-710; containing 10–11 hydroxyethylene units on average, LENEX 698; containing 9 hydroxyethylene units on average). As the alkylpolyether alcohol, there are higher alcohol polyoxyethylene ethers (Triton X-67; CA Registry No. 59030-15-8), etc.

The fluorine-containing polymer microporous membrane may be rendered hydrophilic by providing one or more water-insolubilized water-soluble polymers in its porous spaces. The water-soluble polymers include oxygen-containing hydrocarbons, such as polyacrylamide, polyvinylpyrrolidone, polyvinylamine and polyethylenamine, negative charge-containing ones such as polyvinyl alcohol, polyethylene oxide, polyethylene glycol, methyl cellulose, ethyle cellulose, hydroxyethyl cellulose and hydroxypropyl cellulose, nitrogen-containing ones, such as polyacrylic acid, polymetacrylic acid and polystyrene sulfonic acid, and the like. The water-insolubilization may be conducted by heat treatment, acetal-inducing treatment, esterification, chemical reaction by potassium dichromate, crosslinking by ionizable radiation, or the like. Details are disclosed in Japanese Patent KOKOKU Nos. 56-2094 and 56-16187.

The polysulfone microporous membrane can be prepared by dissolving polysulfone into dioxane, tetrahydrofuran, dimethylformamide, dimethylacetamide, N-methyl-2-pyrolidone or a mixed solvent thereof to obtain a raw liquid for forming film, casting into film by flowing directly into a coagulating solution, washing, and then drying. Details are disclosed in Japanese Patent KOKAI No. 62-27006. In addition, polysulfone microporous membranes are also disclosed in Japanese Patent KOKAI Nos. 56-12640, 56-86941, 56-154051, etc., and they are applicable to the invention. The polysulfone microporous membrane can be rendered hydrophilic, similar to the fluorine-containing polymer, by incorporating surfactant or providing water-insolubilized water-soluble polymer.

As the other nonfibrous microporous membranes, blushed polymer membranes composed of a cellulose ester, such as cellulose acetate, cellulose acetate/butyrate or cellulose nitrate, disclosed in U.S. Pat. No. 3,992,158 or U.S. Pat. No. 1,421,341 are preferable. Microporous membranes of polyamide, such as 6-nylon or 6,6-nylon, or polyethylene, polypropylene, or the like are also usable. Other nonfibrous microporous membranes usable include continuous microspace-containing porous membranes where polymer particulates glass particulates, diatomaceous earth or the like are joined by a hydrophilic or non-water-adsorptive polymer, such as disclosed in U.S. Pat. No. 3,992,158, and U.S. Pat. No. 4,258,001.

Suitable effective pore size of the nonfibrous microporous membrane is 0.2 to 10 $\mu$m, preferably 0.3 to 5 $\mu$m, particularly preferably 0.5 to 5 $\mu$m. The effective pore size of the nonfibrous porous membrane in the invention is the pore size measured by the bubble point method according to ASTM F316-70. In the case that the nonfibrous porous membrane in a membrane filter composed of blushed polymer prepared by the phase separation method, the liquid passages in the thickness direction are, in general, the narrowest at the free surface (glossy face) in the manufacturing process of the membrane, and the pore size in section of each liquid passage stipulated a circle is the smallest near the free surface. The minimum pore size of passages in the thickness direction per unit area has a distribution in facial direction of the membrane filter, and the maximum value determines filtration performance. In general, it is determined by the limit bubble point method.

As mentioned above, in the membrane filter composed of blushed polymer prepared by the phase separation method, liquid passages in the thickness direction become the narrowest at the free surface (glossy face) in the manufacturing process of the membrane. In the case of using the membrane as the nonfibrous porous membrane of the filtering material of the invention, it is preferable to face the glossy face of the membrane filter toward the plasma-discharging side.

A third filtering material may be incorporated into the blood filtering material. The third filtering material may be filter paper, nonwoven fabric, woven fabric such as plain weave fabric, knitted fabric such as tricot fabric, etc. Among them, woven fabric and knitted fabric are preferred. The woven fabric or the like may be treated by glow discharge as disclosed in Japanese Patent KOKAI No. 57-66359. The third filtering material is preferably interposed between the glass fiber filter and the microporous membrane.

Preferable microporous membranes are polysufone membrane, cellulose acetate membrane and the like, and particularly preferred one is polysulfone membrane. In the blood filtering material of the invention, the glass fiber filter is located on the blood inlet side and the microporous membrane in located on the filtrate outlet side.

A suitable thickness of the microporous membrane is about 0.05 to 0.3 mm, preferably about 0.1 to 0.2 mm, and the number of the microporous membrane is usually one. However, two or more sheets of microporous membrane may be used, if necessary.

Instead of or in addition to the microporous membrane, the aforementioned high density glass fiber filter is used. A suitable thickness of the high density glass fiber filter layer is about 0.2 to 1 mm, preferably about 0.3 to 0.7 mm, and may be composed of one sheet of the high density glass fiber filter. However, two or more sheets may be used, if necessary.

The filter device for accommodating the blood filtering material may be any type which is constituted so that the blood to be filtered passes the blood filtering material, and that pressure difference can be added between the blood inlet side and the filtrate outlet side.

However, it is convenient to use a holder which accommodates the blood filtering material, and is provided with a blood inlet and a plasma outlet. The holder is, in general, formed of a body accommodating the blood filtering material and a cap, and every one is provided with at least one aperture. One is used as the blood inlet optionally further a pressurizing port, and the other is used as the plasma outlet, optionally further as a suction port. A suction port may be provided separately. In the case that the holder is rectangular and is provided with the cap on a side of the holder, both of the blood inlet and the plasma outlet may be provided on the holder body.

The volume of the filter chamber which accommodates the blood filtering material is necessary to be greater than the total volume of the blood filtering material both in a dry state and in a swelled state upon absorbing a sample (whole blood). When the volume of the filter chamber is smaller than the total volume of the blood filtering material, filtration does not proceed efficiently and hemolysis occurs. A suitable ratio of the volume of the filter chamber to the total volume of the blood filtering material in a dry state is, in general, 101 to 300%, preferably 110 to 200%, more preferably 120 to 150%, although the ratio varies according to the swelling degree of the filtering material.

Besides, it is preferable that the periphery of the blood filtering material is closely fitted to the wall of the filter chamber so as not to form a bypass of whole blood without passing the filtering material. However, the periphery of glass fiber filter may be not closely fitted but slightly apart from the wall of the filter chamber. In this case, the diameter of microporous membrane, such as polysulfone membrane is made slightly greater than the filter chamber, and the blood cells escaped through the space between the glass fiber filter and the wall of the filter chamber is caught by the microporous membrane.

On assembling the blood filter unit, glass fiber filter, microporous membrane and so on are put in the holder body, and the cap is attached. In the case of using cut pieces of glass fiber filter, they are pressed to the degree that spaces between the cut pieces disappear.

By providing a space on the blood inlet side and filtrate outlet side of the blood filtering material so that the blood filtering material does not adhere to the top and bottom walls of the holder, clogging of the filtering materials and leakage of blood cells can be improved by uniforming blood flow in the blood filtering material. When the cut piece layer is located as the surface layer on the blood inlet side, a screen member, such as a nylon mesh, is provided in order to inhibit the cut pieces from entering the space.

The filter unit of the invention is made into a closed structure except the blood inlet and the filtrate outlet by attaching a cap to the holder body.

As the material of the holder, thermoplastic or thermosetting plastics are preferable. Illustrative of the plastics are high impact polystyrene, methacrylate resin, polyethylene, polypropylene, polyester, nylon, polycarbonate, various copolymers, etc. The material may be transparent or opaque.

Fitting of the cap to the holder body may be any means, such as adhesion using adhesive or fusion welding. On that occasion, either periphery of the holder body or of the cap is located on the inside, or both peripheries are butted. The fitting may be in a state of detachable utilizing screws or the like.

The shape of the blood filtering material is not restricted, but disc and polygon is preferable in view of production. By rendering the size of the blood filtering material slightly greater than the inside section of the holder body (i.e. filter chamber), breakthrough of blood at the periphery of the filtering material can be prevented.

The first characteristic of the method of the invention is to keep the pressure difference between the blood inlet side and the filtrate outlet side 50 mmHg or less at least for 5 seconds after supplying blood to be filtered, exactly from the contact of the blood with the glass fiber filter layer. A preferable pressure difference in the first step is 30 mmHg or less, and natural spreading of the blood is also preferred. A preferable keeping time is 10 seconds or more.

A suitable supply amount of blood is about 1.2 to 5 times, preferably 2 to 4 times the volume of blood filtering material, and against the volume of the low density glass fiber filter, a suitable supply amount is about 1.2 to 3 times, preferably 1.2 to 2 times.

After the above first step, blood filtration is accelerated by sucking from the filtrate outlet side and/or pressurizing from the blood inlet side. A convenient suction or pressurizing means is to use a peristallic pump or a syringe. The second characteristic of the invention is to restrict the pressure difference between the blood inlet side and the filtrate outlet side to 200 mmHg or less. A preferable maximum pressure difference is 170 mmHg, particularly preferably 150 mmHg. The lower limit of the pressure difference is not restricted, but in the viewpoint of practical filtration speed, it is preferable to keep the pressure difference 30 mmHg or more, more preferably 50 mmHg or more. In the case of using a syringe, a preferable travel distance of piston is that the travel volume of the piston is about 2 to 5 times the volume of blood filtering material. A suitable travel speed is about 1 to 500 ml/cm$^2$·min, preferably about 20 to 100 ml/cm$^2$·min.

Incidentally, hematocrit value of blood greatly varies, and thereby, filtration resistance (elevation speed of pressure difference according to pressurizing or reducing pressure varies. That is, when pressure is increased or decreased at a constant speed, in the case of blood having a great hematocrit value, pressure difference rapidly increases to bring sharp decrease of filtration speed caused by clogging of filtering material or breakage of blood cells caused by the addition of great pressure difference prior to obtaining a desired amount of plasma or serum. On the other hand, in the case of blood having a small hematocrit value, filtration speed is too great, and leakage of blood cells occurs. Thereupon, it is preferable to suck and/or pressurize at a definite speed pattern after supplying blood to filtering material, to trace pressure difference variation between the blood inlet side and the filtrate outlet side with time, to estimate the hematocrit value of the filtering blood based on the detected pressure difference, and to adjust thereafter the suction and/or pressurizing speed. The above definite speed pattern is in general a constant speed, but any other definite speed pattern is also applicable. The adjustment of suction and/or pressurizing speed according to the hematocrit value is, in the case of high hematocrit value blood, to keep the variation rate of suction and/or pressurizing small and to lower the maximum pressure reduction rate (to lengthen the time for filtration), because hemalysis is liable to occur. In the case of low hematocrit value blood, the adjustment is to add relatively high suction and/or pressurizing speed, because hemolysys scarcely occurs and filtration is easily carried out.

An actual process is to determine an optimum pattern of suction pressure and suction period as to various whole blood samples different in hematocrit value. Since the hematocrit value of a blood sample to be filtered is not known, suction is started according to the suction pattern of a standard blood (e.g. hematocrit value: 45%), and the hematocrit value of the blood sample is estimated by the variation with time and the difference from the standard value. Then, filtration is continued, while the suction pressure an suction period are adjusted so as to meet the optimum pattern. This process is also applicable to the case of pressure filtration.

EXAMPLES

Example 1

(1) Preparation of Holder

Figure 3:
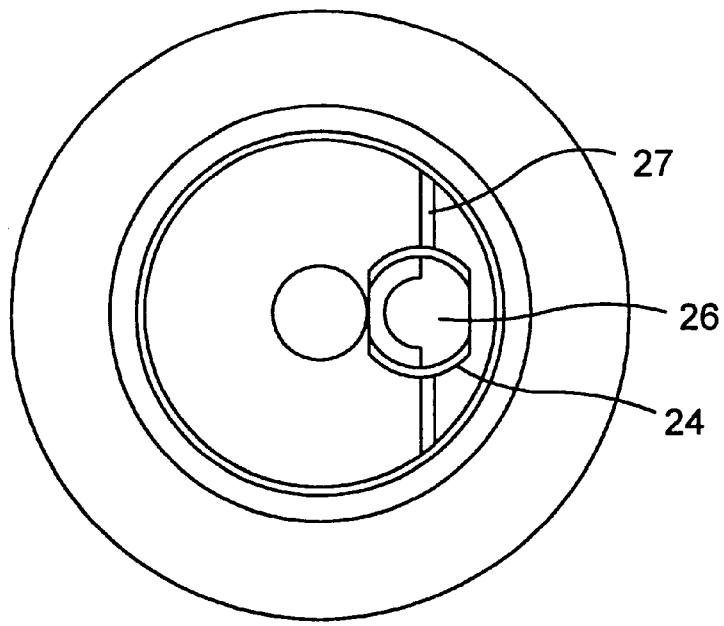
FIG. 3 is a plan view.
Figure 4:
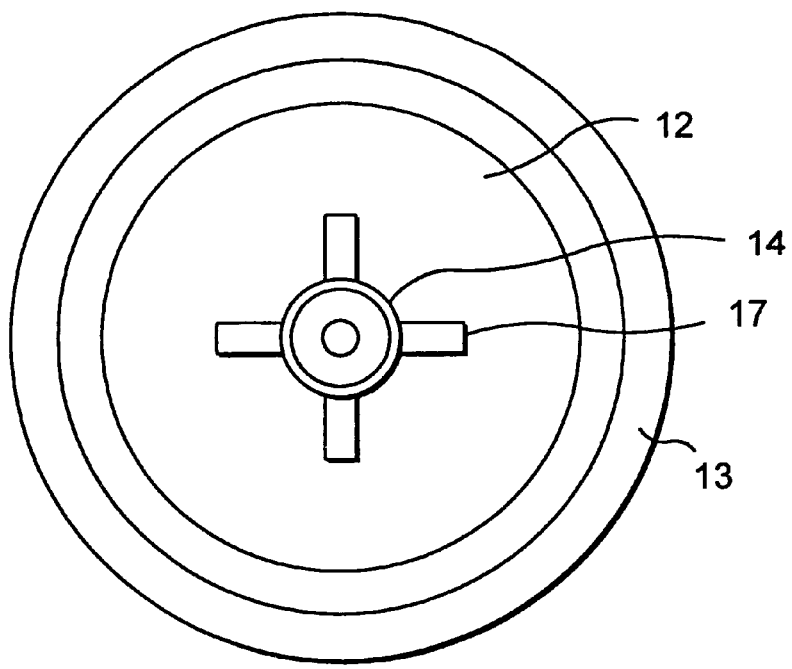
FIG. 4 is a bottom view thereof.

A blood filter unit illustrated in FIGS. 2–4 was prepared. The filter unit was composed of a holder body 10 and a cap 20, as shown in FIG. 2 which illustrates an assembled state of the filter unit.

The holder body 10 is formed of a filter chamber 11 (diameter: 20.1 mm) for accommodating blood filtering material(s) 30 and a flange 13 formed outward at the upper end of the filter chamber 11. The bottom of the filter chamber 11 is made by a thin funnel-shaped circle plate portion 12 with a step portion near the periphery, and a nozzle-shaped blood inlet 14 is extended downward from the center of the circle plate portion 12. The above step portion functions as a spacer 16 for separating the underside of the blood filtering material 30 from the funnel-shaped circle plate portion 12 to form a space 15. As shown in FIGS. 2 and 4, flaps 17 are formed on the base portion of the blood inlet 14 toward four directions. The flaps 17 are for holding a sample tube (not illustrated) containing blood by fitting thereto.

The underside of the bottom of the cap 20 is recessed to form an upper space wherein 4 steps 21 are formed in a concentric circle shape. Five projection 25 are projected downward as the means for preventing adhesion in the central portion in the shape of 5 spots in a die. A plasma passage 24 in a smokestack-shaped with shaving in parallel stands upward from near the middle point between the center and periphery, and a pent-roof 26 which prevent spouting upward of discharged plasma is provided at the top of the plasma passage 24 in the horizontal direction. As shown in FIG. 3, the pent-roof 26 has a shape of a combination of two half circles. The half circle on the periphery side is in consistent with the outer wall of the plasma passage 24, and the half circle on the center side is in consistent with extension of the inner wall of the plasma passage 24. A partition wall 27 is formed in straight interposing the plasma passage in order to ensure a sufficient depth even in a small plasma volume. The upper end of the plasma receiver 22 is opened, and it becomes a suction port 28. A flange 23 is formed outward near the lower end of the cap 20, and the flange 23 is joined to the flange 13 of the holder body by ultrasonic welding. A rib (not illustrated) is formed on the face of the flange 23 facing the flange 13 of the holder body so as to ensure liquid-tight ability at the joined portion.

(2) Assembling of Filter Unit

Six sheets of glass fiber filter (GF/D, Whatman) punched into disc 20.3 mm in diameter were superposed and put in the holder body 10 (inside diameter: 20.1 mm) made of plastic. A sheet of polysulfone microporous membrane 33 (SE-200, Fuji Photo Film Co., Ltd.) 170 μm in thickness punched into disc 20.7 mm in diameter was put thereon. The cap 20 was fitted to the holder body 10, and both flanges 13, 23 were welded to be sealed by ultrasonic welding. A nozzle (Fuji Clean Tip, Fuji Photo Film Co., Ltd.) was attached as the nozzle for sucking blood to the blood inlet 14 to complete the filter unit.

(3) Collection of Blood 10 ml of vein blood was drawn from a healthy man using a vacuum blood collection tube containing heparin (Terumo). The hematocrit value of the blood was measured and found to be 44%. Each 3 ml of the blood was put in three 4 ml plastic test tubes.

(4) Suction Apparatus

A compact suction apparatus was prepared which was connected to a peristallic pump of which the exhaust velocity was variable. A suction adapter made of silicone rubber which was connectable to the suction port of the filter unit under airtight conditions was attached to the end of the tube of the compact suction apparatus. A gauge for monitoring pressure was connected to the midway of the tube.

(5) Filtration of Blood

The nozzle for sucking blood of the filter unit was inserted into the blood collected in item (2), and the other end of the filter unit was connected to the suction adapter of the suction apparatus. The exhaust velocity of the suction apparatus was adjusted so that the pressure reduction degree reached 100 mmHg after 30 seconds, and suction was continued. The pressure reduction degree after 10 seconds was 30 mmHg.

(6) Recovery of Plasma

Plasma was streamed into the plasma receiver with the proceeding of suction. The amount of the plasma was 330 μl. The color of the plasma was light yellow, and hemolyzate and contamination of red blood cells were not observed.

(7) Evaluation of Filtrate

In order to evaluate the contamination degree of each plasma by hemolyzate quantitatively, LDH activity of each plasma was measured by using a clinical assay analyzer ("Fuji Drichem 5500", Fuji Photo Film Co., Ltd.). In a comparison, LDH activity of the plasma obtained by centrifuging was also measured. The results are shown in Table 1.

TABLE 1

| | Hct | LDH Activity of Plasma (IU/L) | |
|---|---|---|---|
| | (%) | Invention | Centrifuging |
| Sample-1 | 39 | 116 | 117 |
| Sample-2 | 44 | 134 | 131 |
| Sample-3 | 47 | 164 | 162 |

Example 2

Experiments similar to Example 1 were carried out according to various suction patterns shown in FIG. 1. The results are shown in Table 2.

TABLE 2

| Pattern | Variation of Pressure Reduction Degree with Time | | | Maximum Pressure | | Recovery | | Quality of Plasma | |
|---|---|---|---|---|---|---|---|---|---|
| | Former Period | Middle Period | Latter Period | Reduction Degree | Suction Period | Middle Hct | High Hct | Middle Hct | High Hct |
| A | La | Sm | Sm | La | Sh | Δ | X | Δ | X |
| A' | La | Sm | Sm | M | | Δ | X | Δ | X |
| B | M | La | Sm | | Sh | Δ | X | Δ | X |
| C | M | M | M | La | M | ○ | Δ | ○ | Δ |
| D | Sm | M | M | La | M | ○ | ○ | ○ | ○ |
| E | Sm | Sm | Sm | Sm | Lo | ○ | ○ | ○ | ○ |

La: Large
M: Middle
Sm: Small
Lo: Long
Sh: Short

As can be seen from the results of Table 2, plasmas with good quality can be obtained by keeping pressure reduction degree low at initial stage of suction.

Example 3

In an experiment similar to Example 1, suction filtration was carried out with monitoring the degree of pressure reduction. The hematocrit value of the blood subjected to the experiment was 43%. Recovered plasma was 320 μl, and hemolysis and contamination of blood cells were not observed at all.

The suction pattern was set as follows:
Time from Start of Suction (sec) 0 10 20 30
Degree of Pressure Reduction (mmHg) 0 30 110 170
Suction was conducted at a low speed for 10 seconds from the start of suction, and then elevated to a middle speed for 20 seconds of the latter period.

Various components of the plasma were measured using a Hitachi 7150 analyzer. In a comparison, components of the plasma obtained from the same blood by centrifuging were measured. The results are shown in Table 3.

TABLE 3

| Item | Unit | Centrifuged | Filtered | Judgement |
|---|---|---|---|---|
| Na | mEg/L | 141.8 | 141.9 | ◉ |
| K | | 4.31 | 4.39 | ◉ |
| Cl | | 104.8 | 106.3 | ◉ |
| ALB | mg/dl | 4.33 | 4.27 | ◉ |
| TBIL | | 0.35 | 0.34 | ◉ |
| BUN | | 23.2 | 23.2 | ◉ |
| Ca | | 9 | 8.8 | ◉ |
| TG | | 78 | 74 | ◉ |
| CRE | | 1.06 | 1.05 | ◉ |
| TCHO | | 142 | 136 | ◉ |
| GLU | | 102 | 106 | ◉ |
| TP | | 7.18 | 7.03 | ◉ |
| UA | | 3.8 | 3.74 | ◉ |
| ALP | IU/L | 143 | 136 | ◉ |
| AMYL | | 78 | 78 | ◉ |
| CPK | | 83 | 82 | ◉ |
| GGT | | 18 | 18 | ◉ |
| GOT | | 13.4 | 13.3 | ◉ |
| GPT | | 9.1 | 7.3 | ◉ |
| LDH | | 99 | 105 | ◉ |
| CRP | | 0 | −0.07 | ◉ |
| LAP | | 47 | 48 | ◉ |
| IP | | 2.9 | 3 | ◉ |
| CKMB | | 7.8 | 8.3 | ◉ |
| CHE | | 220 | 214 | ◉ |
| HDL | mg/dl | 611 | 59.4 | ◉ |

Example 4

In an experiment similar to Example 3, a mechanism of detecting the degree of pressure reduction, monitoring the variation, and feeding the time when the degree of pressure reduction reaches 170 mmHg to the operating system of the suction apparatus was incorporated into the suction apparatus.

40 ml of blood with heparin of healthy person having a hematocit value of 48% was drawn, and used in the following experiments.

In the case of the blood of healthy person, the time requiring that the degree of pressure reduction reaches 150 mmHg was 25 seconds or more. In the case of the blood having a hematocrit value of 50% or more, the degree of pressure reduction reached 150 mmHg shorter than 25 seconds conversely.

That is, for example, in the case of the, whole blood of which the hematocrit value was adjusted to 55%, the degree of pressure reduction reached 150 mmHg after 22.5 seconds. The time that the degree of pressure reduction reaches 150 mmHg was detected, and in the case of high hematocrit value blood, the suction period was lengthened with keeping the degree of pressure reduction at 170 mmHg. As a result, even in the case of high hematocrit value blood samples exceeding the hematocrit value of 50%, a desired amount of plasmas with good quality could be obtained.

We claim:

1. A method of filtering blood using a filtering material comprising a glass fiber filter and a microporous membrane, the method comprising keeping an initial pressure difference between a blood inlet side of the filtering material and a filtrate outlet side of the filtering material of 50 mm Hg or less for at least 5 seconds after contacting the blood to be filtered with the blood inlet side, then controllably increasing the pressure difference while keeping an overall pressure difference between the blood inlet side and filtrate outlet side of 200 mm Hg or less throughout filtering of the blood, and achieving a final pressure difference between the blood inlet side and the filtrate outlet side of at least 50 mm Hg upon completion of the filtering of the blood.

2. The method of filtering blood of claim 1 which further comprises measuring pressure differences between the blood inlet side and the filtrate outlet side, and applying at least one of suction and pressure at a controlled rate to maintain the initial pressure difference at 50 mm Hg or less and the overall pressure difference at 200 mm Hg or less.

3. The method of filtering blood of claim 1 wherein said glass fiber filter has a density of 0.05 g/cm$^3$ to 0.13 g/cm$^3$.

4. The method of filtering blood of claim 1 wherein said microporous membrane is a polysulfone microporous membrane.

5. The method of filtering blood of claim 1 comprising keeping an intially pressure difference of 30 Hg or less.

6. The method of filtering blood of claim 1 comprising keeping an overall pressure difference of 170 mmHg or less.

7. The method of filtering blood of claim 1, wherein the microporous membrane has a thickness of 0.05 mm to 0.3 mm.

* * * * *